US 9,687,252 B2

United States Patent
Kelman et al.

(10) Patent No.: US 9,687,252 B2
(45) Date of Patent: Jun. 27, 2017

(54) FEMORAL REAMING SYSTEM AND METHOD OF PERFORMING TRIAL REDUCTION

(71) Applicant: Smith & Nephew, Inc., Memphis, TN (US)

(72) Inventors: David C. Kelman, Somerville, TN (US); Terry W. McLean, Eads, TN (US); Richard D. Lambert, Collierville, TN (US); Vincent W. Shotton, Magnolia, TX (US); David A. Harwood, New Brunswick, NJ (US); Alisha W. Bergin, Olive Branch, MS (US); Jerry L. Jones, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/611,436

(22) Filed: Feb. 2, 2015

(65) Prior Publication Data
US 2015/0320427 A1   Nov. 12, 2015

Related U.S. Application Data

(62) Division of application No. 12/282,467, filed as application No. PCT/US2007/063733 on Mar. 9, 2007, now abandoned.

(Continued)

(51) Int. Cl.
| | |
|---|---|
| *A61B 17/16* | (2006.01) |
| *A61B 17/88* | (2006.01) |
| *A61F 2/36* | (2006.01) |

(52) U.S. Cl.
CPC ........ *A61B 17/1617* (2013.01); *A61B 17/164* (2013.01); *A61B 17/1668* (2013.01);
(Continued)

(58) Field of Classification Search
CPC .................................................. A61B 17/164
(Continued)

(56) References Cited

U.S. PATENT DOCUMENTS

| | | | |
|---|---|---|---|
| 5,201,882 A | 4/1993 | Paxson | |
| 5,607,431 A * | 3/1997 | Dudasik | ................ A61B 17/15 606/102 |

(Continued)

FOREIGN PATENT DOCUMENTS

| | | |
|---|---|---|
| DE | 2542056 A1 | 3/1977 |
| WO | 94/27507 A | 12/1994 |

(Continued)

OTHER PUBLICATIONS

International Search Report; European Patent Office; International PCT Application No. PCT/US2007/063733; Jan. 1, 2008; 4 pages.

(Continued)

*Primary Examiner* — Samuel Hanna
(74) *Attorney, Agent, or Firm* — Taft Stettinius & Hollister LLP (57) ABSTRACT

An apparatus (10) for removing bone material comprises a distal cutting instrument (12) and a proximal cutting instrument (14). The distal cutting instrument has at least one first cutting edge (30), a shoulder (20), and a shaft portion (22). The shaft portion (22) has an anti-rotation feature. The at least one first cutting edge (30) removes bone material when moved in a first direction. The proximal cutting instrument (14) is removably attached to the shaft portion (22). The proximal cutting instrument (14) has a first end portion (68) and a second end portion (66). The second end portion (66) contacts the shoulder (20) of the distal reamer (12) when the proximal reamer is mounted to the shaft portion (22). The proximal reamer (14) has at least one second cutting edge (32) and an aperture. The aperture is adapted to receive the (Continued)

anti-rotation feature of the shaft portion (22) of the distal reamer (12). The at least one second cutting edge (32) removes bone material when moved in a second direction.

15 Claims, 10 Drawing Sheets

Related U.S. Application Data (60) Provisional application No. 60/826,675, filed on Sep. 22, 2006, provisional application No. 60/781,025, filed on Mar. 10, 2006.

(52) U.S. Cl.
CPC .............. *A61B 17/162* (2013.01); *A61B 17/88* (2013.01); *A61F 2002/3625* (2013.01)

(58) Field of Classification Search
USPC .......................................................... 606/80
See application file for complete search history.

(56) References Cited

U.S. PATENT DOCUMENTS

| | | | |
|---|---|---|---|
| 5,908,423 A * | 6/1999 | Kashuba | A61B 17/164 408/127 |
| 6,117,138 A | 9/2000 | Burrows et al. | |
| 6,206,884 B1 | 3/2001 | Masini | |
| 6,283,970 B1 | 9/2001 | Lubinus | |
| 6,517,581 B2 | 2/2003 | Blamey | |
| 7,001,392 B2 | 2/2006 | McGovern | |
| 7,074,224 B2 | 7/2006 | Daniels et al. | |
| 7,235,106 B2 | 6/2007 | Daniels et al. | |
| 2003/0204262 A1 | 10/2003 | Ferguson et al. | |
| 2004/0122525 A1 | 6/2004 | Daniels et al. | |
| 2004/0193168 A1 | 9/2004 | Long et al. | |
| 2004/0267266 A1 | 12/2004 | Daniels et al. | |
| 2004/0267267 A1 * | 12/2004 | Daniels | A61B 17/1617 606/80 |
| 2005/0203527 A1 * | 9/2005 | Carrison | A61B 17/1604 606/80 |
| 2005/0234462 A1 | 10/2005 | Hershberger | |
| 2005/0234463 A1 | 10/2005 | Hershberger et al. | |
| 2005/0234470 A1 | 10/2005 | Hershberger | |

FOREIGN PATENT DOCUMENTS

| | | |
|---|---|---|
| WO | 96/24313 A | 8/1996 |
| WO | 2007106752 A2 | 9/2007 |
| WO | 2009046121 A2 | 4/2009 |

OTHER PUBLICATIONS

Canadian Office Action; Canadian Patent Office; Canadian Patent Application No. 2,645,150; Mar. 12, 2015; 3 pages.
Written Opinion; International Searching Authority; International PCT Application No. PCT/US2008/078470; Apr. 15, 2009; 4 pages.
Search Report; International Searching Authority; International PCT Application No. PCT/US2008/078470; Apr. 15, 2009; 3 pages.

* cited by examiner

FEMORAL REAMING SYSTEM AND METHOD OF PERFORMING TRIAL REDUCTION

CROSS-REFERENCE TO RELATED APPLICATIONS

This application is a divisional of Application No. 12/282,467, which is the National Stage of International Application No. PCT/US2007/063733, filed Mar. 9, 2007, and which claims the benefit of U.S. Provisional Applications No. 60/826,675, filed Sep. 22, 2006 and No. 60/781,025 filed Mar. 10, 2006. The disclosure of each application is incorporated by reference in its entirety.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

This invention relates generally to surgical devices and, more particularly, to surgical devices used in long bones.

2. Related Art

Current modular implant instrument systems are such that there are two separate reamers provided in preparing the femoral canal. One reamer is used to prepare the distal portion of the canal. The reamer is then removed from the drill and the second reamer is attached to the drill to prepare the proximal portion of the canal. Such systems are labor intensive and time consuming.

Other systems build on or add to the distal reamers. In these systems, the surgeon would have to build the reamer before attaching to the drill. The surgeon is typically required to ream with the distal reamer until the desired distal diameter is achieved. At this point the surgeon has to remove the distal reamer from the drill and add the proximal reamer/s from the end of the distal reamer shaft. In this system, both the proximal reamer and distal reamer have their own depth marks to reference the greater trochanter. Neither reamer has a common reference mark between the reamers. Therefore, the reamers may still be inexact in preparing the distal to proximal portions of the femoral canal because of errors such as tolerance stack and human error. With the addition of sleeves, another tolerance (sleeve length) must be taken into account when reaming the proximal depth.

Yet another example uses a combination proximal and distal reamer (or plurality of reamers) having a flexible core within the reamer to allow the proximal portion to flex and prepare the medial side of the metaphyseal within the femur. It can also be utilized to fit more within the bow of the femur. This flexible core can create a series of potential issues. First issue is the ability to clean the tool core. With spiral cuts within the core or other means to create flexibility, the potential exists for blood, tissue, or small bone fragments to be caught within the core of the reamer. Another issue is with the potential of the system binding such that the flexible core creates a "coiling" effect and doesn't allow the reamers to turn and cut due to more torsional resistance of the bone cutting than torsional resistance of the flexible core.

For a proximal reamer design, the shaft drives both the proximal and distal reamers simultaneously. The elongated shaft guides the proximal broach to remove the medial side of the metaphyseal. Therefore, the purpose of having the modular proximal reamer is to have exposure for the elongated shaft to use as a guide in broaching.

In other embodiments, the distal reamer is utilized for reaming out the distal segment only. The surgeon disconnects the distal reamer and connects to a proximal reamer. The proximal reamer requires a distal pilot to be attached, for guiding purposes during the preparation of the metaphyseal for the implant.

Other reamers have a trial head/neck that can be attached to a reamer or broach for a trial reduction. The head/neck trial assembly is attached by a handle to create the version desired. The head/neck assembly can also be adjusted proximally or distally to select the desired height as well. The location of the head/neck assembly relative to the reamer or broach may be difficult to replicate with the implant. There are no references to locate the head/neck assembly in locating height, thus the implant does not necessarily reflect what the surgeon measured during the trial reduction. The surgeon has to somewhat guess and estimate where the implant will be located and place the head/neck assembly to that location accordingly.

Other systems with a distal reamer, proximal reamer, and trial neck utilize guide channels on the trial neck adaptor to establish anti-rotation and implant orientation. The proximal reamer is required to have straight flutes in order to have guide channels. The guide channels dictate the cutting geometry that can be utilized for the proximal reamer. This system also does not facilitate the ability for the proximal and distal reamers to be modular such that a surgeon can have various proximal reamers for a given distal reamer.

There remains a need in the art for increasing accuracy while decreasing the number of steps/instruments that is required of systems that utilize proximal/distal reaming systems. In addition, accuracy and decreasing the number of steps may also be achieved with respect to the method of performing a trial reduction for modular implant designs.

In addition, orienting the trial neck in situ without having to remove the reamer construct, especially in small incisions, may be beneficial.

SUMMARY OF THE INVENTION

In one aspect of the invention, an apparatus for removing bone material comprises a distal cutting instrument and a proximal cutting instrument. The distal cutting instrument has at least one first cutting edge, a shoulder, and a shaft portion. The shaft portion has an anti-rotation feature. The at least one first cutting edge removes bone material when moved in a first direction. The proximal cutting instrument is removably attached to the shaft portion. The proximal cutting instrument has a first end portion and a second end portion. The second end portion contacts the shoulder of the distal reamer when the proximal reamer is mounted to the shaft portion. The proximal reamer has at least one second cutting edge and an aperture. The aperture is adapted to receive the anti-rotation feature of the shaft of the distal reamer. The at least one second cutting edge removes bone material when moved in a second direction.

In another embodiment of the invention, the at least one first cutting edge is a right-hand cutting flute, and the at least one second cutting edge is a left-hand cutting flute.

In another embodiment of the invention, the apparatus further comprises a quick connect assembly. The quick connect assembly is mountable to the shaft portion and adapted to contact the first end portion.

In another embodiment of the invention, the quick connect assembly further comprises a depth guide reference.

In another embodiment of the invention, the apparatus further comprises a trial neck mountable to the shaft portion and adapted to contact the first end portion.

In another embodiment of the invention, the apparatus further comprises a trial neck mountable to the distal cutting instrument.

In another embodiment of the invention, the apparatus further comprises a trial neck mountable to the proximal cutting instrument.

In another embodiment of the invention, the proximal cutting instrument has a slot that extends an entire length of the proximal cutting instrument.

In another embodiment of the invention, the anti-rotation feature comprises a square cross-section.

In another embodiment of the invention, the trial neck further comprises a modular portion. The modular portion is configured to be received within the trial neck.

In another embodiment of the invention, the modular portion is further configured to have a tapered portion. The tapered portion allows for adjustment of the neck axis of the trial neck.

In another embodiment of the invention, the first cutting instrument comprises a broach.

In another embodiment of the invention, the apparatus further comprises an insertion tool configured to attach the trial neck to the cutting instruments.

In another embodiment of the invention, the trial neck and the first end portion of the proximal cutting instrument are further configured having a circumferential pattern of ridges and valleys. The ridges of the pattern on the trial neck are configured to mate to the valleys of the pattern on the first end portion of the proximal cutting surface.

In another embodiment of the invention, the insertion tool is further configured to rotate the trial neck relative to the distal and proximal cutting instruments.

In yet another aspect of the invention, a system for performing a trial reduction comprises a combination cutting instrument and a trial neck. The combination cutting instrument comprises a distal cutting instrument and a proximal cutting instrument. The distal reamer has at least one first cutting edge, a shoulder, and a shaft portion. The shaft portion has an anti-rotation feature. The at least one first cutting edge removes bone material when moved in a first direction. The proximal cutting instrument is removably attached to the shaft portion. The proximal cutting instrument has a first end portion and a second end portion. The second end portion contacts the shoulder when the proximal cutting instrument is mounted to the shaft portion. The proximal cutting instrument has at least one second cutting edge and an aperture. The aperture is adapted to receive the anti-rotation feature. The at least one second cutting edge removes bone material when moved in a second direction. The modular trial neck is operatively connected to the combination cutting instrument.

Another aspect of the invention provides a method for performing a trial reduction comprising providing a combination cutting instrument having a distal cutting instrument and a proximal cutting instrument. The distal reamer has at least one first cutting edge, a shoulder, and a shaft portion. The shaft portion has an anti-rotation feature. The at least one first cutting edge removes bone material when moved in a first direction. The proximal cutting instrument is removably attached to the shaft portion. The proximal cutting instrument has a first end portion and a second end portion. The second end portion contacts the shoulder when the proximal cutting instrument is mounted to the shaft portion. The proximal cutting instrument has at least one second cutting edge and an aperture. The aperture is adapted to receive the anti-rotation feature. The at least one second cutting edge removes bone material when moved in a second direction. The modular trial neck is operatively connected to the combination cutting instrument. Bone material is removed by moving the combination cutting instruments in the first direction and in the second direction. A modular trial neck is attached to the combination cutting instrument. A trial reduction of the implant is performed.

In yet another aspect of the invention, a method of preparing a long bone for an implant comprises cutting a distal portion of the long bone by moving a first cutting instrument in a first direction. Another step provides coupling a second cutting instrument to the first cutting instrument. A proximal portion of the long bone is cut by moving the coupled cutting instruments in a second direction different from the first direction such that when the first cutting instrument is moved in the second direction, the first cutting instrument does not cut the distal portion of the long bone.

Another aspect of the invention provides a method for preparing a trial insert for a long bone. The method comprises preparing a canal in the long bone using at least one cutting instrument. The cutting instrument has the shape of the trial insert. The method also comprises adjusting a trial neck relative to the cutting instrument and coupling the trial neck to the cutting instrument. The trial neck may then be sized relative to the acetabulum for proper version of the trial implant.

The invention has several advantages over prior devices and techniques. First, the devices may increase accuracy while decreasing the number of steps/instruments that is required of systems that utilize proximal/distal reaming systems. Increased accuracy may reduce the amount of natural bone removed from the femur and may reduce the amount of further preparation after the initial reaming. In addition, reducing the number of steps and instruments may reduce total operation time.

Second, increased accuracy and decreased number of steps may also be achieved with respect to the method of performing a trial reduction for modular implant designs, at least partially because the trial neck may be oriented in situ without having to remove the reamer construct.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
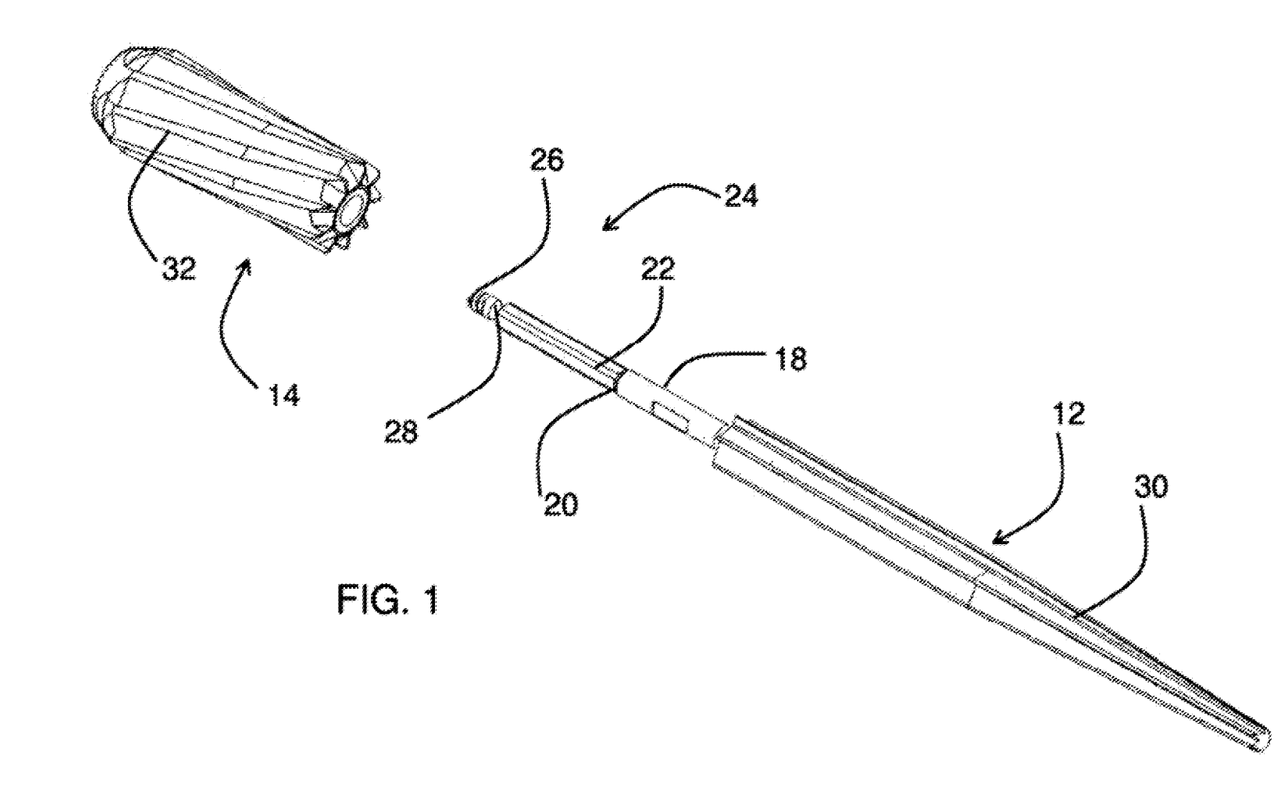
FIG. 1 is an exploded view of parts of a femoral reamer according to an embodiment of the invention.

Referring to the accompanying drawings in which like reference numbers indicate like elements, FIG. 1 is an exploded view of parts of a femoral reamer 10 according to an embodiment of the invention. The femoral reamer 10 includes two major components, a distal reamer 12 and a proximal reamer 14. The distal reamer 12 prepares the femur for receiving a stem of a femoral implant and the proximal reamer 14 prepares the femur for receiving a sleeve of a femoral implant. The distal reamer 12 includes a thick depth shaft 18, a shoulder 20, a distal reamer shaft 22 and a quick connect mating portion 24. The quick connect mating portion 24 includes a mounting tip 26 and a groove 28. The quick connect mating portion 24 is attached to a drill.

The distal reamer 12 includes right-hand cutting flutes 30 while the proximal reamer 14 includes left-handed cutting flutes 32. The right-handed cutting flutes 30 have edges on the flutes that cut in a forward cutting action when the reamer 10 is rotated. The edges of the flutes of the distal reamer 12 cuts bone in preparing the distal aspects of the femur by connecting the reamer 10 at the quick connect mating portion 24 to a drill. The reamer 10 may cut the femur in a clockwise manner. The surgeon will ream up (starting at smaller diameters) to the desired distal diameter based on pre-operative templating. In conjunction, the surgeon will ream to a depth based on the implant size. While this embodiment describes one way in which the distal and proximal reamers may be moved relative to one another, those having ordinary skill in the art understand that other relative motions, such as switching the directions of the flutes 30 and 32 or combining axial motion and rotational motion may be implemented. After preparing the distal femur, the proximal femur may be prepared.

In order to prepare the proximal portion of the femur, the distal reamer 12 is disconnected from the drill and the proximal reamer 14 is attached to the distal reamer 12. The proximal reamer 14 may be slid onto the shaft 22 of the distal reamer 12. The shaft 22 of the distal reamer 12 may have a square cross-section to engage with a square aperture within the proximal reamer 14. The shaft 22 may transfer torque and rotation from the distal reamer 12 to the proximal reamer 14. The proximal reamer 14 may be advanced on the distal reamer 12 until the proximal reamer 14 rests upon the shoulder 20 of the depth shaft 18. The depth shaft 18 sets the relative depth of the distal reamer 12 to the proximal reamer 14. The depth shaft 18 may be larger in diameter in order to minimize stresses on the distal reamer 12.

In other embodiments, the cross section of the shaft 22 and the aperture in the proximal reamer 14 may be other shapes which allow the proximal reamer 14 to be coupled to the shaft 22 of the distal reamer 12. The cross-section of the shaft 22 provides for anti-rotation of the proximal reamer 14 relative to the distal reamer 12. When the cross-section is in the shape of a square, then there are four possible rotational orientations of the proximal reamer 14 relative to the distal reamer 12 in which the proximal reamer 14 may be seated on the shaft 22. Other cross-sectional embodiments, such as a hexagon or octagon, would have 6 and 8 possible rotational orientations of the proximal reamer 14 relative to the distal reamer 12, respectively. Other cross-sectional shapes, such as a star shape, may also transfer torque and rotation to the proximal reamer 14.

The proximal femur is prepared using the proximal reamer 14. The surgeon may ream up (starting at a small diameter proximal reamer 14) the proximal portion of the femur by rotating the drill in a counterclockwise manner. The edges of the flutes 32 of the proximal reamer 14 are left-handed cutting flutes. When the reamer 10 is rotated counterclockwise, the left-handed cutting flutes 32 cut the proximal femur. However, the distal reamer 12, when rotated counterclockwise, does not cut the distal femur because the edges of the right-handed cutting flutes 30 of the distal reamer 12 only cut the distal femur when the reamer 10 is rotated clockwise. When rotated counterclockwise, the distal reamer 12 acts as a guide to prepare the proximal femoral canal minimizing additional bone being removed distally. Pre-operative templating may determine the final proximal reamer diameter. In conjunction, the surgeon will ream to a depth based on the implant size. In addition, the distal reamer 12 may limit the depth of the proximal reamer 14 and act as a guide for the orientation of the proximal reamer 14.

In another embodiment, the proximal reamer may include a slot that runs through the overall length of the proximal reamer. The slot allows the proximal reamer to be "side-loaded" onto a distal reamer without disconnecting the distal reamer from the drill. In such an embodiment, the proximal reamers contain left-hand cutting flutes so that the drill must be set to reverse in order for the proximal reamer to cut. By using a side loading distal reamer, sizing changes between smaller diameter and larger diameter proximal reamers may also be made without disconnecting the distal reamer from the drill.

A side loaded proximal reamer may be attached to the distal reamer by two parallel flats on the shaft of the distal reamer. The flats, in combination with the slot of the proximal reamer, allow for the proximal reamer to be indexed and locked in position with the aid of a spring loaded plunger. The spring loaded plunger may overlap a portion of the proximal reamer to form an interference fit between the proximal reamer and distal reamer. While the flats may transfer torque and rotation from the distal reamer to the proximal reamer, an interference fit may hold the proximal reamer in axial alignment with the distal reamer.

In operation, the combination reamer 10 allows for variable reaming size during distal and proximal femur preparation, according to the size of the implant used in the femur. By maintaining the distal reamer position during proximal reaming, fewer stack errors from referencing points relative to other points may be achieved. For example, angular offsets between the proximal and distal portions are minimized, as well as linear offsets such as depth or lateral movement. Any eccentricity between the shape of the reamer and the shape of the relief may be minimized because less jitter may result when only one of the distal or proximal reamers cuts at one time. This may result in less total bone removal by more accurately removing only the bone necessary to remove. In addition, the orientation may allow for better placement of the implant within the femoral canal with more uniform contact between the implant and the natural bone.

The quick connect mating portion 24 includes the mounting tip 26 and the groove 28. The groove 28 is an indentation in the shaft 22 and is configured to receive a ball bearing as described in FIG. 2. The mounting tip 26 may have a cross-section similar to the distal reamer shaft 22, or may have a cross-section smaller than the shaft 22. However, the cross-section of the mounting tip 26 should be larger than the cross-section of the groove 28. The mounting tip 26 may be threaded so that a trial implant may be attached to the distal reamer 12. In other embodiments, the mounting tip may be configured with other fasteners for attaching the distal reamer 12 to the trial implant.

Figure 2:
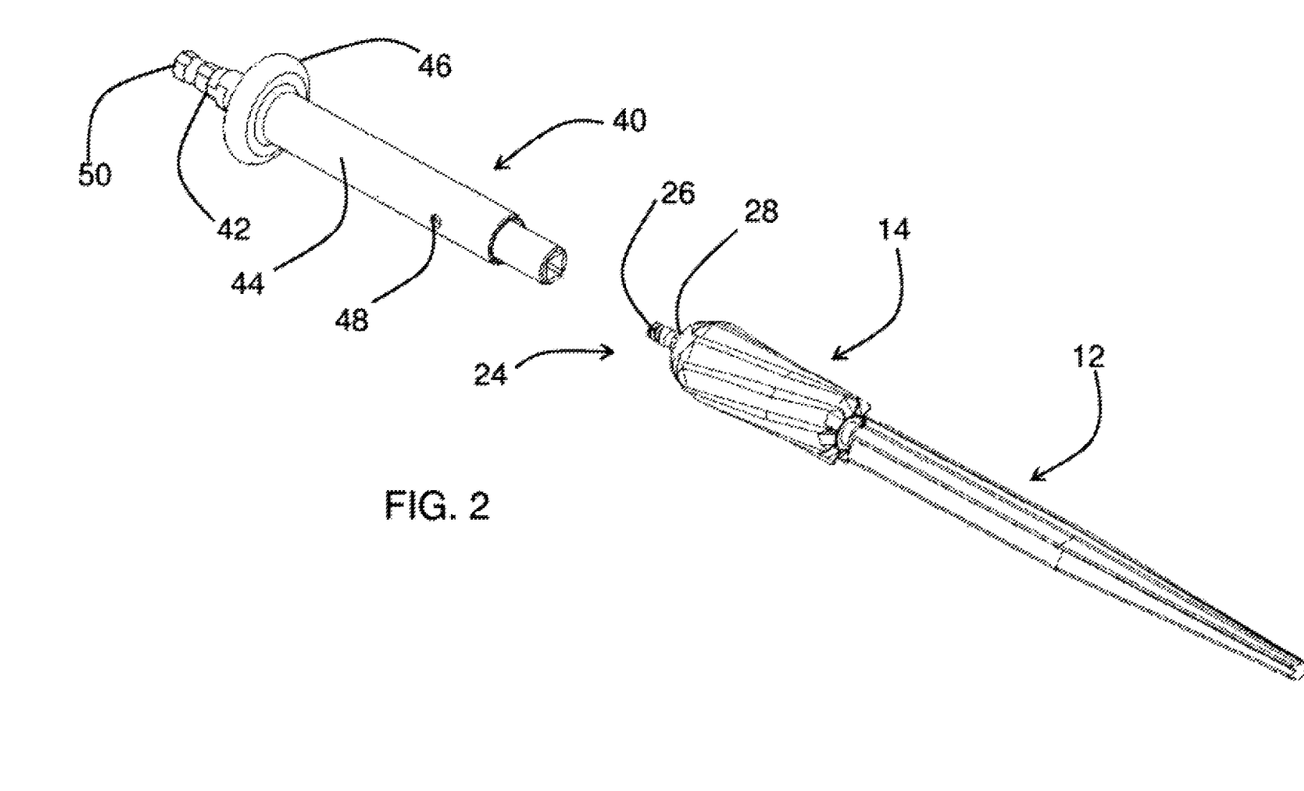
FIG. 2 is an exploded view of the parts of FIG. 1 and a quick connect assembly.

Turning now to FIG. 2, FIG. 2 is an exploded view of the parts of FIG. 1 and a quick connect assembly 40. The quick connect assembly 40 includes an inner cylinder 42, an outer cylinder 44, a flange 46, a transverse pin 48 and a drill connector 50. The inner cylinder 42 is axially slidable within the outer cylinder 44, and is biased at the transverse pin 48. The transverse pin 48 is fixed axially to the outer cylinder 42 and extends through the outer and inner cylinders 42 and 44. The pin extends through the inner cylinder 42 within a slot. The slot also houses a spring which biases the drill connector 50 of the inner cylinder 42 axially away from the flange 46.

When the inner cylinder 42 is axially slid within the outer cylinder 44 (i.e., the drill connection 50 is depressed toward the flange 46), a pair of bearings are slid out of the bottom of the quick connect assembly 40. The bearings extend radially outward from the quick connect assembly 40 to a distance greater than the inner diameter of the outer cylinder 44. With the bearings extending out from the inner cylinder 42, the quick connect assembly 40 is positioned to connect to the reamers 12 and 14.

The proximal reamer 14 is seated on the distal reamer 12. When the proximal reamer 14 is seated on the distal reamer 12, the mounting tip 26 and the groove 28 are located above the proximal reamer 14. Thus, the mating portion 24 of the distal reamer 12 is positioned for attachment to the quick connect assembly 40. The quick connect assembly 40 is slid over the mounting tip 26 and the groove 28. The bearings, extended outward, are slid over the groove 28. The drill connection 50 of the inner cylinder 42, then, may be axially slid away from the flange 46 and the bearings forced into the groove 28 by the inner surface of the outer cylinder 44. The inner cross-section of the inner cylinder 42 may be shaped like the cross-section of the distal reamer shaft 22 so that the torque and rotation from the drill may be transferred from the quick connect assembly 40 to the reamers 12 and 14.

When the quick connect assembly 40 is attached to the reamers 12 and 14, the depth of the distal reamer 12 is fixed relative to the quick connect assembly 40. The quick connect assembly 40 may secure a tight axial fit of the proximal reamer 14 between the quick connect assembly 40 and the distal reamer 12. In addition, whether the proximal reamer 14 is attached to the distal reamer 12 does not change the depth of the distal reamer 12. Because the distance is fixed, the quick connect assembly 40, then, may also have indicator lines for each implant size on the quick connect assembly 40. These indicator lines may reference the tip of the greater trochanter, and may be etched into the visible portions of the inner or outer cylinders 42 and 44. Thus, the quick connect assembly 40 may act as a single reference guide for both the distal reamer 12 and the proximal reamer 14.

Figures 3A, 3B:
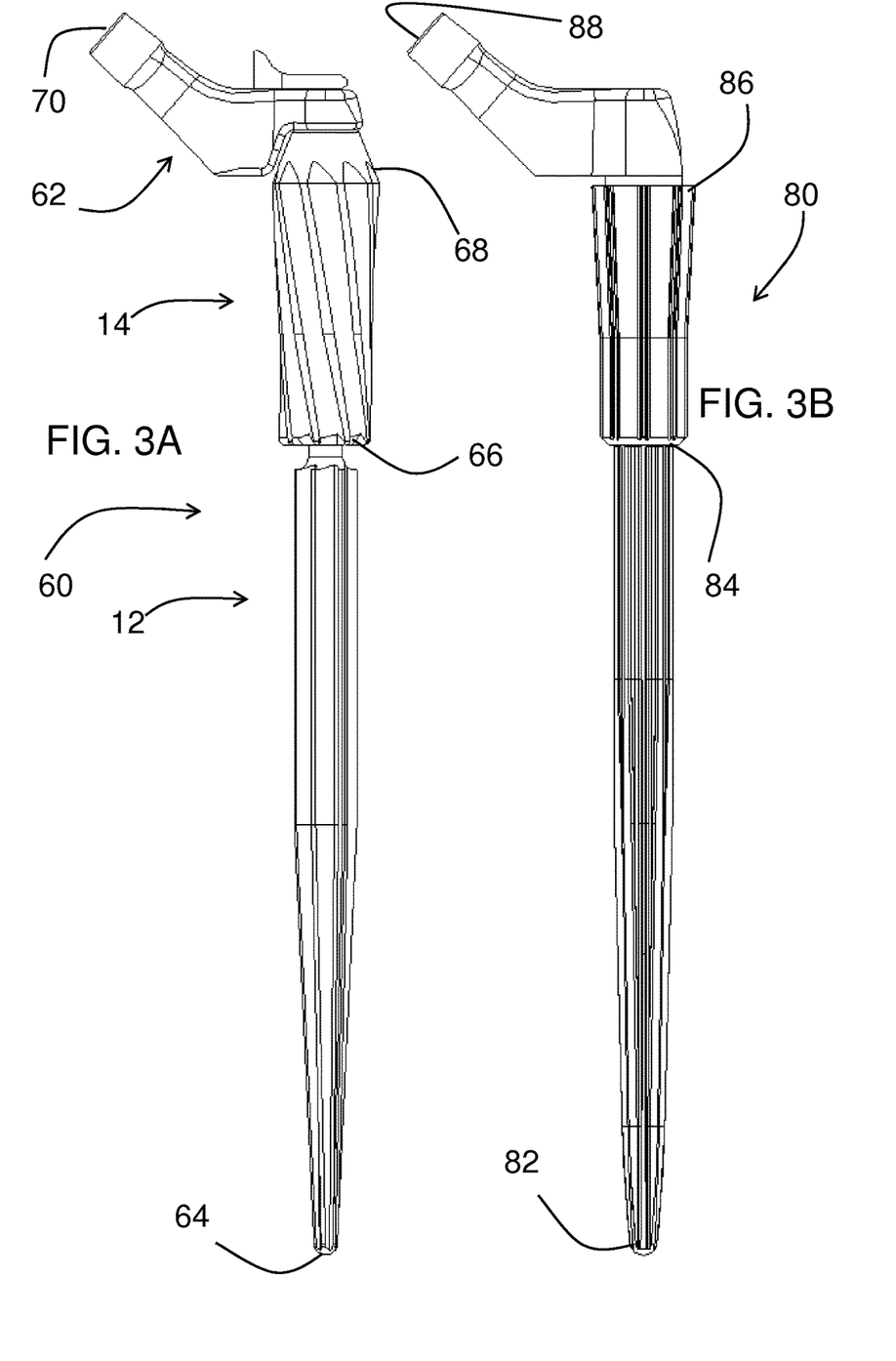
FIG. 3A is a view of a trial femoral implant including the parts of the femoral reamer of FIG. 1.
FIG. 3B is a view of a femoral implant.

Turning now to FIG. 3A, FIG. 3A is a view of a trial femoral implant 60 including parts of the femoral reamer of FIG. 1. The trial implant 60 includes the distal reamer 12, the proximal reamer 14 and a trial neck 62. The trial neck 62 is oriented relative to the reamers 12 and 14 similar to the orientation of the neck of an implant. When attached to the reamers 12 and 14, the trial neck 62 acts as an implant for correctly positioning the femoral component relative to the acetabular component of the implant.

After proximal and distal reaming is complete, the quick connect assembly is detached from the shaft of the distal reamer 12. The proximal and distal reamers are still located within the femoral canal. The trial neck 62 is then connected to the shaft of the distal reamer 12, to the proximal reamer 14, or any combination of the two. The trial neck 62 may be angularly oriented about the axis of the femur, thus providing the surgeon with the desired version angle for the implant prosthesis. The surgeon may then perform a trial reduction of the implant by using the proximal and distal reamers 14 and 12 in conjunction with attaching a trial head to the trial neck 62.

Figure 4A:
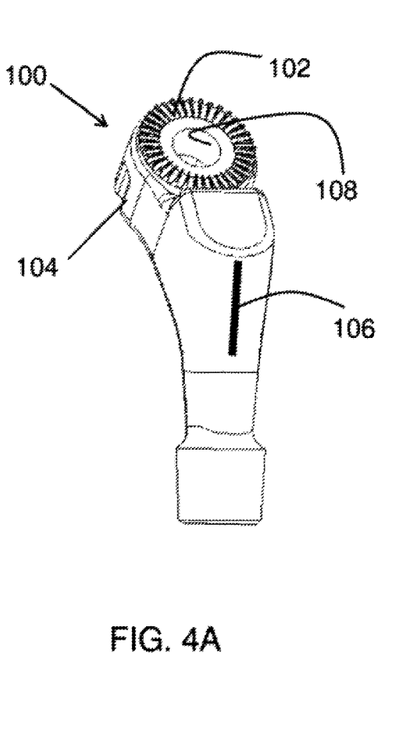
FIGS. 4A and 4B are views of trial necks according to an aspect of the invention.
Figure 4B:
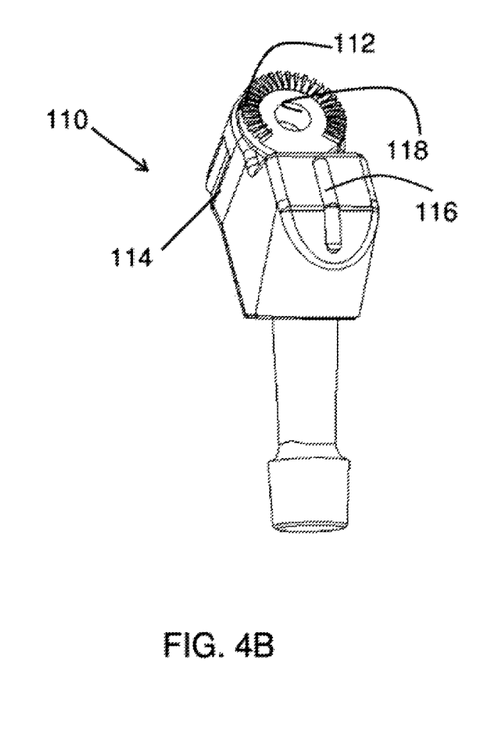

The trial neck 62 may be attached to the distal reamer 12 at the mounting tip. For example, a threaded connector may be used through an aperture, as shown in FIGS. 4A and 4B of the trial neck 62, to fix the trial neck 62 to the reamers 12 and 14. When the trial neck 62 is attached, the distance from a tip 64 of the distal reamer 12 to the trial neck 62 is fixed. Similarly, a shoulder 66 and upper flared portion 68 of the proximal reamer 14 as well as a head 70 of the trial neck 62 are also fixed in orientation and position relative to one another. These positions and orientations also match the positions and orientations of an implant, as shown in FIG. 3B.

Turning now to FIG. 3B, FIG. 3B is a view of a femoral implant 80. A distal tip 82 of the femoral implant 80, a distal shoulder 84, a flared proximal shoulder 86, and a neck head 88 partially define the geometry of the implant 80. The geometry of the implant 80 is approximated by the trial 62 of FIG. 3A. The proximal reamer 12 reams to a depth equivalent to the depth of the tip 82 of the implant 80. The proximal reamer 14 approximates the shape of the implant 80 between the distal and proximal shoulders 84 and 86. The fixed head 88 of the implant 80 is approximated by the trial head 70. As discussed below, the ability to orient and size the trial head 70 allows for proper implantation of the implant 80.

Turning now to FIGS. 4A and 4B, FIGS. 4A and 4B are views of trial necks 100 and 110 according to an aspect of the invention. The trial necks 100 and 110 include a poker chip mating surface 102 and 112, recessed portions 104 and 114, and cavities 108 and 118. The trial neck 100 of FIG. 4A includes an alignment guide 106, and the trial neck 110 of FIG. 4B includes a fin 116.

The poker chip mating surfaces 102 and 112 are adjustable in rotational orientation relative to the reamers. The mating surfaces 102 and 112 are formed such that when the surfaces 102 and 112 are mated to like surfaces on a reamer or other part of the trial implant, the ridges on the trial necks 100 and 110 are seated within the valleys of the like surfaces on the reamer. Similarly, the valleys on the trial necks 100 and 110 are seated within the ridges of the like surfaces on the reamer. The trial neck, 100 or 110, then, may be rotated about a general central axis of the reamers. The patterns of the poker chip surface 102 and 112 may be any general surface that allows for a plurality of positions in which to fix the trial neck 100 or 110 to the reamers. In addition, the pattern does not have to be complete around the cavities 108 and 118.

The cavities 108 and 118 are configured to receive a connector in order to compress the trial necks 100 and 112 to the reamers, respectively. A connector, such as a T-nut, may be used to fix the trial necks 100 and 110 to the threaded connector of the distal reamer. The trial neck, then, is screwed in place between the connector and the reamer. Thus, when connected by a connector, the trial neck 100 or 110 may be fixed in place for trial reduction. The orientation of the trial neck 100 or 110 may be adjusted by using a tool mated to the recesses 104 and 114 to rotate the trial head 100 and 110.

The recesses 104 and 114 may be similar to a spanner head of a screw. The recesses 104 and 114 receive prongs from a tool (shown in FIGS. 7-10) which may provide rotation to the trial head. By placing the recesses 104 and 114 on the periphery of the trial necks 100 and 110, minimal torque may be used to rotate the trial neck. In addition, the peripheral placement of the recesses 104 and 114 may minimize interference with the connector used through the cavities 108 and 118 to fix the trial necks 100 and 110 to the reamers. While the spanner head-like design of the recesses 104 and 114 have been used in this example, other interfaces designed to transfer rotation and torque from a tool to the trial head 100 or 110 may be used.

The trial necks 100 and 100 may also have certain features that help orient the neck relative to the bony anatomy. Features such as the groove 106 or fin 116 may be used as a guide to cauterize or draw reference marks on the anatomical structures or natural features to reference the position of the trial neck 100 or 110 relative to other anatomical landmarks or structures.

Rotation of the trial neck 100 or 110 may be limited by an anti-rotational element to prevent rotation of the trial neck with respect to the bone. The element may be a fin such as the fin 116, spike, screw, or other structure or method that engages the bone to prevent rotation of the trial neck 100 or 110. Likewise, the proximal and distal reamers may have structures or methods to prevent rotation of the trial implant relative to the bone. This may be accomplished by, for example, a collar fitted over the reamers to prevent rotation, screws projecting into the bone, grooves that accept pins or screws placed between the trial implant and the bone, or any other structure or method to prevent rotation. The methods and structures that provide rotational alignment of the reamer may also be used as a way to match the alignment of the implant to the trial and associated reamers.

Figure 5:
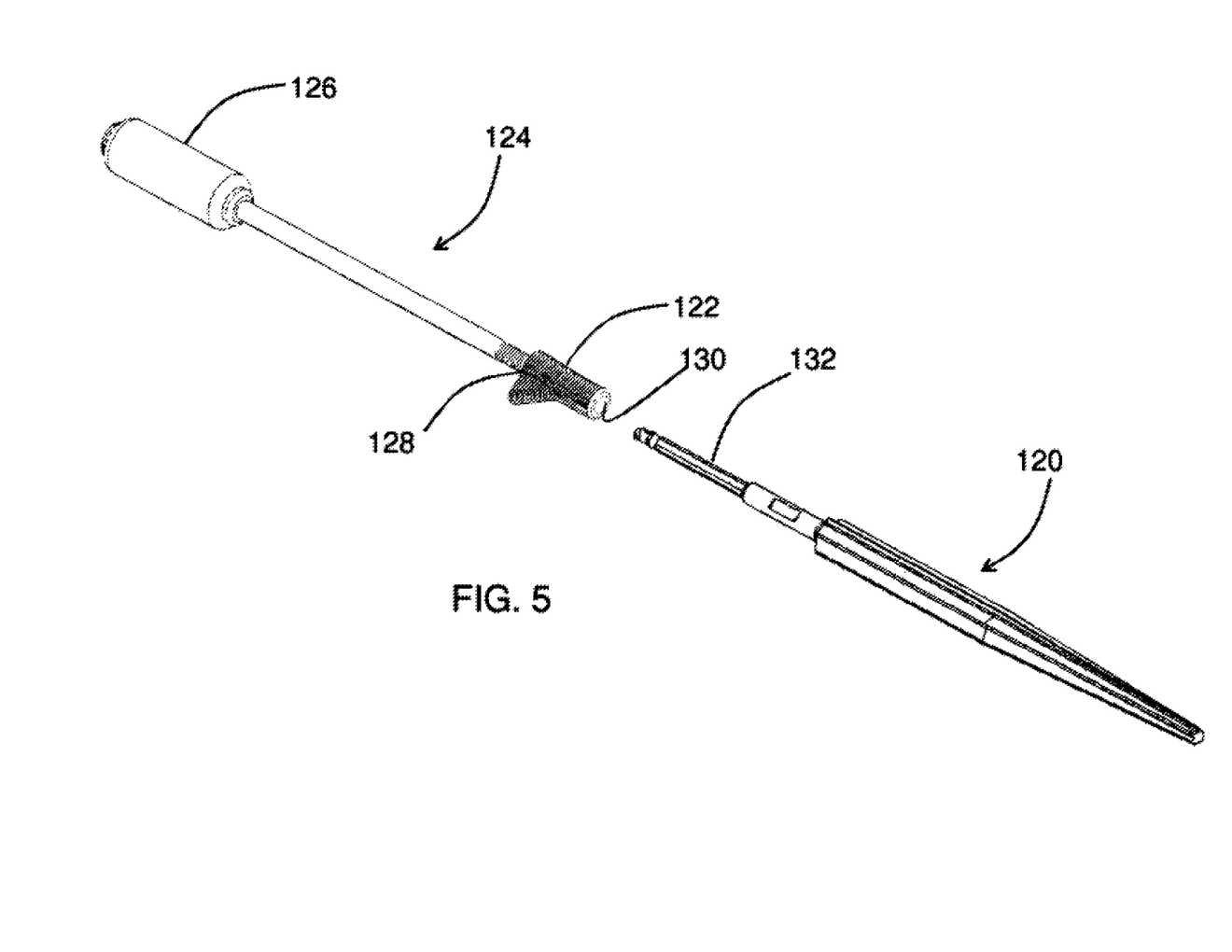
FIG. 5 is an exploded view of a distal femoral reamer and a proximal broach according to an embodiment of the invention.

Turning now to FIG. 5, FIG. 5 is an exploded view of a distal femoral reamer 120 and a proximal broach 122 according to an embodiment of the invention. The broach 122 is configured to connect to an impactor tool 124, which includes a handle 126 and a connector 128. The broach 122 and the tool 124 have a cavity 130 configured to receive a shaft 132 of the distal reamer 120. The shaft 132 aligns the proximal cutting instrument 122 along the axis of the distal reamer 120. The handle 126 allows a surgeon to manipulate the broach 122 from the end of the tool 124. The connector 128, in this embodiment a threaded portion of the tool 124, is configured to receive the broach 122, or other cutting instrument. Because the broach 122 is not integral to the tool 124, the size of the broach 122 may be changed according to the needed relief for the implant.

The cutting instruments (the distal reamer 120 and the broach 122, in this embodiment) provide another method of preparing a portion of the bone. Other cutting instruments such as rasps or files may be used to remove bone so that the shape in relief approximates the shape of an implant. The cutting instruments may use the distal cutting instrument (in this example, the distal reamer) as a guide. The cutting instruments may prepare any number of geometries either symmetrical or asymmetrical. The instrument may have any number asymmetrical features such as spouts, fins, or bodies.

Figure 6:
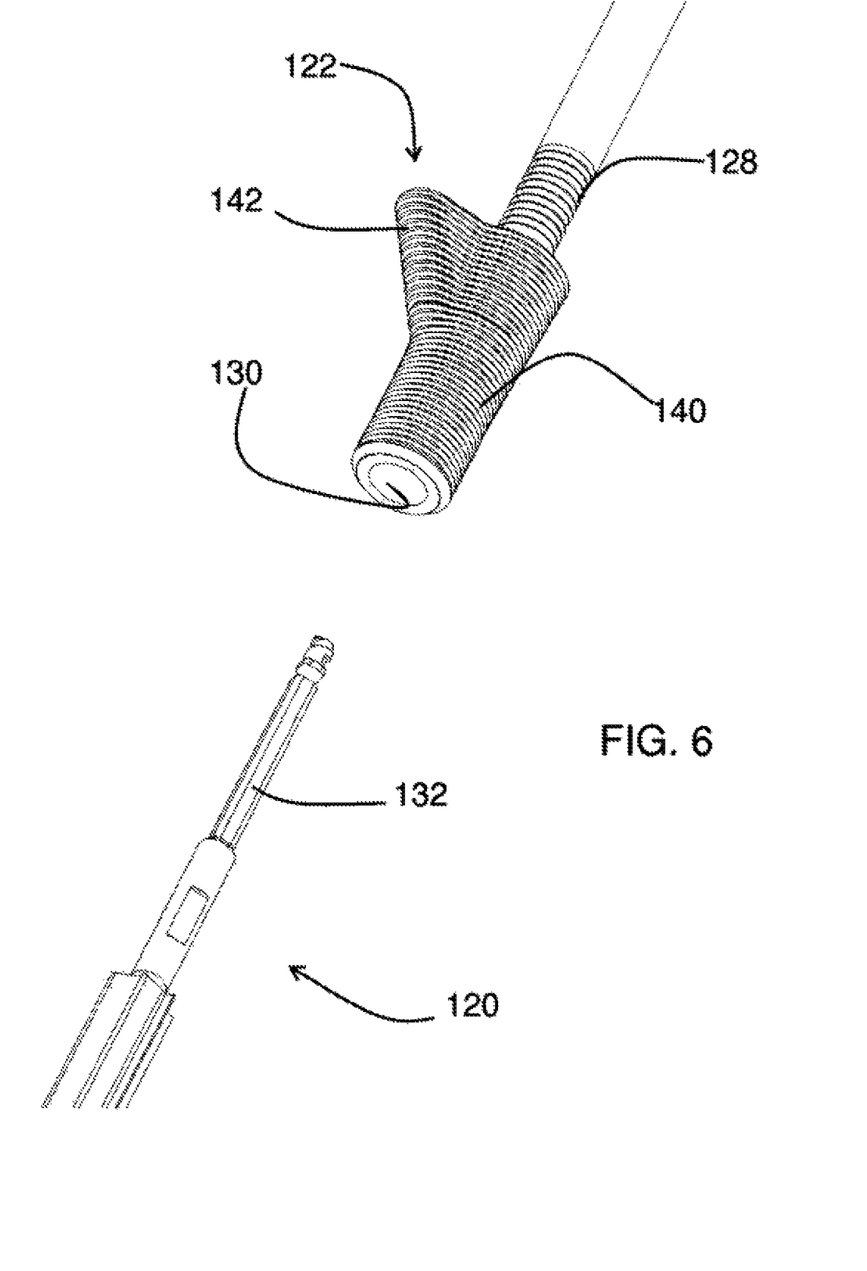
FIG. 6 is a close-up view of the distal femoral reamer and the proximal broach of FIG. 5.

Turning now to FIG. 6, FIG. 6 is a close-up view of the distal femoral reamer 120 and the proximal broach 122 of FIG. 5. As described previously, the shaft 132 of the distal reamer 120 is received within the cavity 130 to guide the broach 122 along the axis of the distal reamer 120. The threaded portion 128 of the tool connects the tool to the broach 122. Cutting edges 140 of the broach 122 cut the proximal bone when the broach 122 is moved axially along the shaft 132. The cross-section of the shaft 132, which in this embodiment is square, keeps the broach 122 from rotating. Rotation would cause an asymmetrical section 142 to rotate and remove more bone than desired.

The cutting edges 140 of the broach 122 may be circumferential edges separated axially along the axis of the broach 122. The cutting edges 140 may also extend around the asymmetrical portion 142 of the broach 122 to allow for cutting an asymmetrical relief into the bone. While the cutting edges of the broach 122 in this embodiment are circular, other patterns for the cutting edges, such as spiral edges, may be used on the broach 122.

Figure 7:
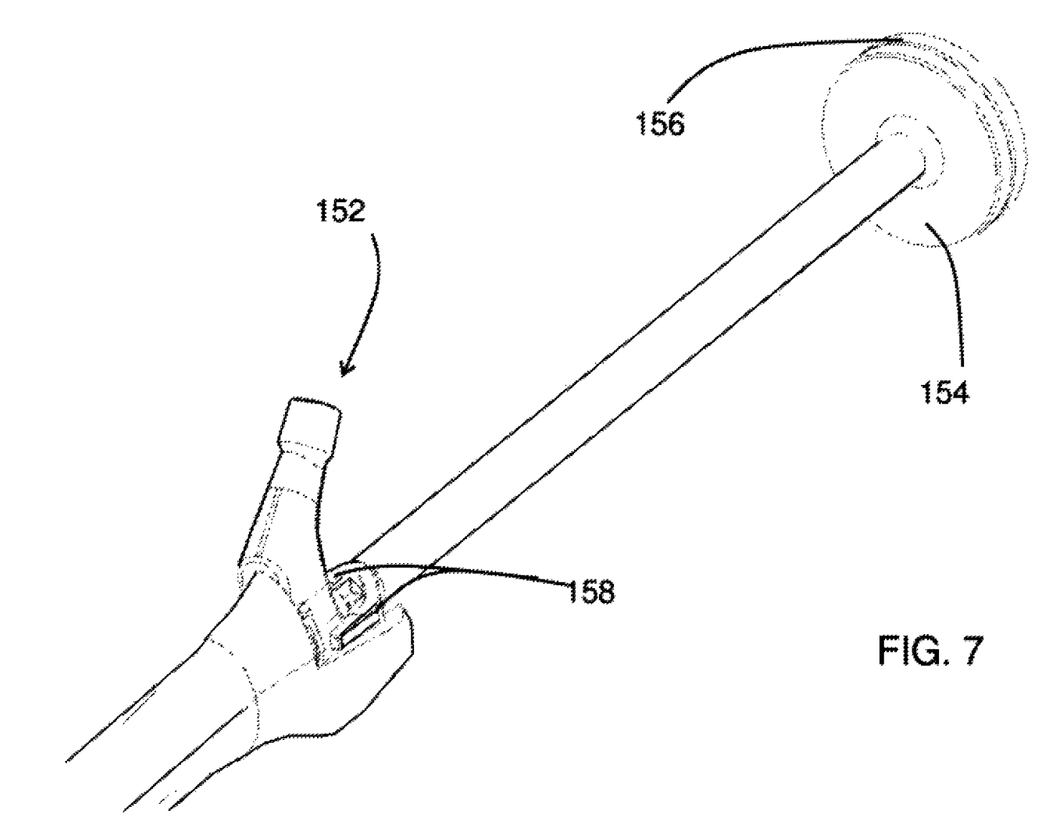
FIG. 7 is a view of an insertion tool inserting a trial into a femur according to an aspect of the invention.

Turning now to FIG. 7, FIG. 7 is a view of an insertion tool 150 inserting a trial 152 into a femur according to an aspect of the invention. The insertion tool 150 includes an outer member 154 and an inner member 156. The outer member 154 includes prongs 158 configured to rotate the trial. The tool 150 may reference the position or version of the trial neck to the bone with the position and orientation of the prongs 158. Features may reference certain anatomical landmarks or prepositioned landmarks such as cautery marks or pin anchors, or to instruments either part of the construct or in the surgical field.

The inner member 156 includes a portion configured to fix the trial 152 to the reamers. The portion of the inner member 156 may include a driver head configured to interface with a screw head on the trial 152. As previously described, the screw head would connect to the mounting tip of the distal reamer through the cavity in the trial neck to fix the trial neck 152 to the reamer.

The prongs 158 of the outer member 154 attach to the recesses on the trial head to rotate the trial neck 152 within the femoral canal. In order to adjust the trial neck 152, the tool 150 is used to release the trial neck connection from the reamer. The tool 150 may hold, reposition, and reconnect the trial neck 152. Likewise the tool 150 may also introduce or remove the trial neck from the surgical field.

Figure 8:
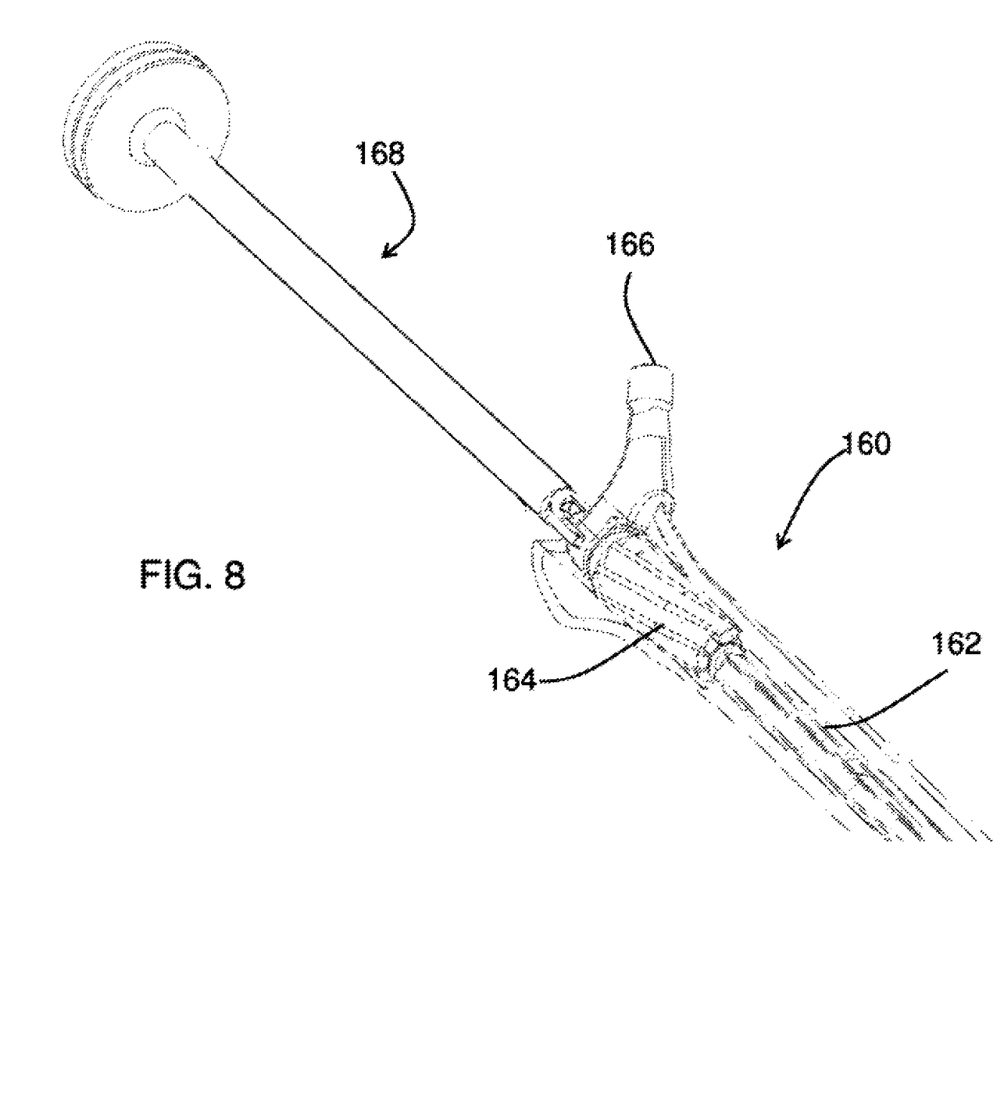
FIG. 8 is a cut-away view of the femur of FIG. 7 showing the trial.

Turning now to FIG. 8, FIG. 8 is a cut-away view of the femur of FIG. 7 showing the trial. 160. The trial 160 is axially aligned through the distal reamer 162, the proximal reamer 164, the trial neck 166 and the insertion tool 168. The relative orientation of the insertion tool 168 to the reamers 162 and 164 sets the version and orientation of the trial neck 166 for the trial 160. Thus, the trial 160 may be made up of the reamers 162 and 164 and a trial neck 166, allowing for a modular sizing, versioning, and orienting of the implant by allowing multiple sizes of trial heads and versions of trial heads in a single step.

Figure 9:
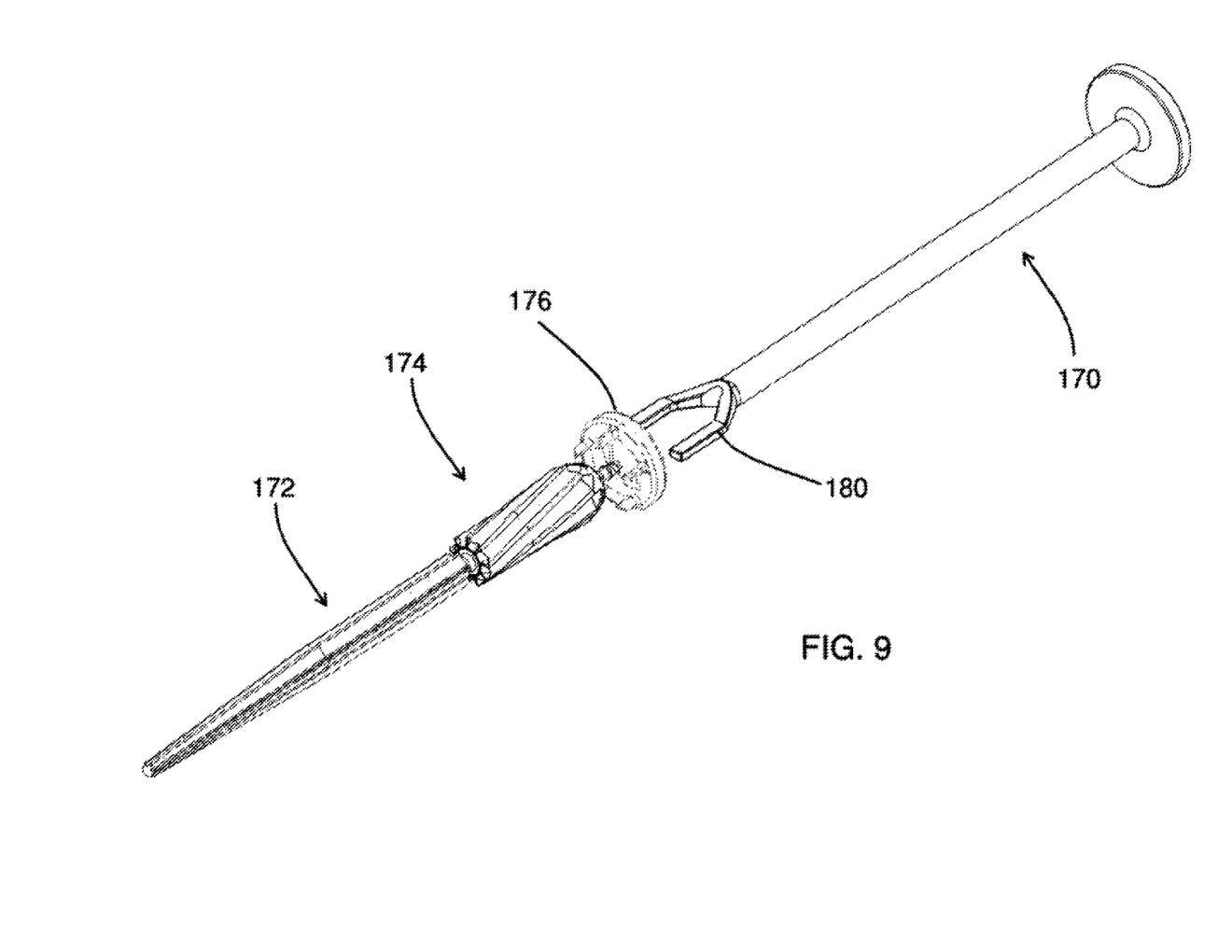
FIG. 9 is a view of an insertion tool according to an aspect of the invention.

Turning now to FIG. 9, FIG. 9 is a view of an insertion tool 170 according to an aspect of the invention. A distal reamer 172, a proximal reamer 174 and a sleeve impactor ring 176 are aligned with the tool 170. Prongs 180 impact the impactor ring 176, which would impact a proximal sleeve. A trial neck may also be attached to the modular implant sleeve impactor 176, for example through a quick connect assembly to the sleeve impactor 176. By disconnecting the impaction portion of the sleeve impactor 176, the trial neck may be connected. Thus, the surgeon can perform a trial reduction including a proximal sleeve implant.

Figures 10A, 10B:
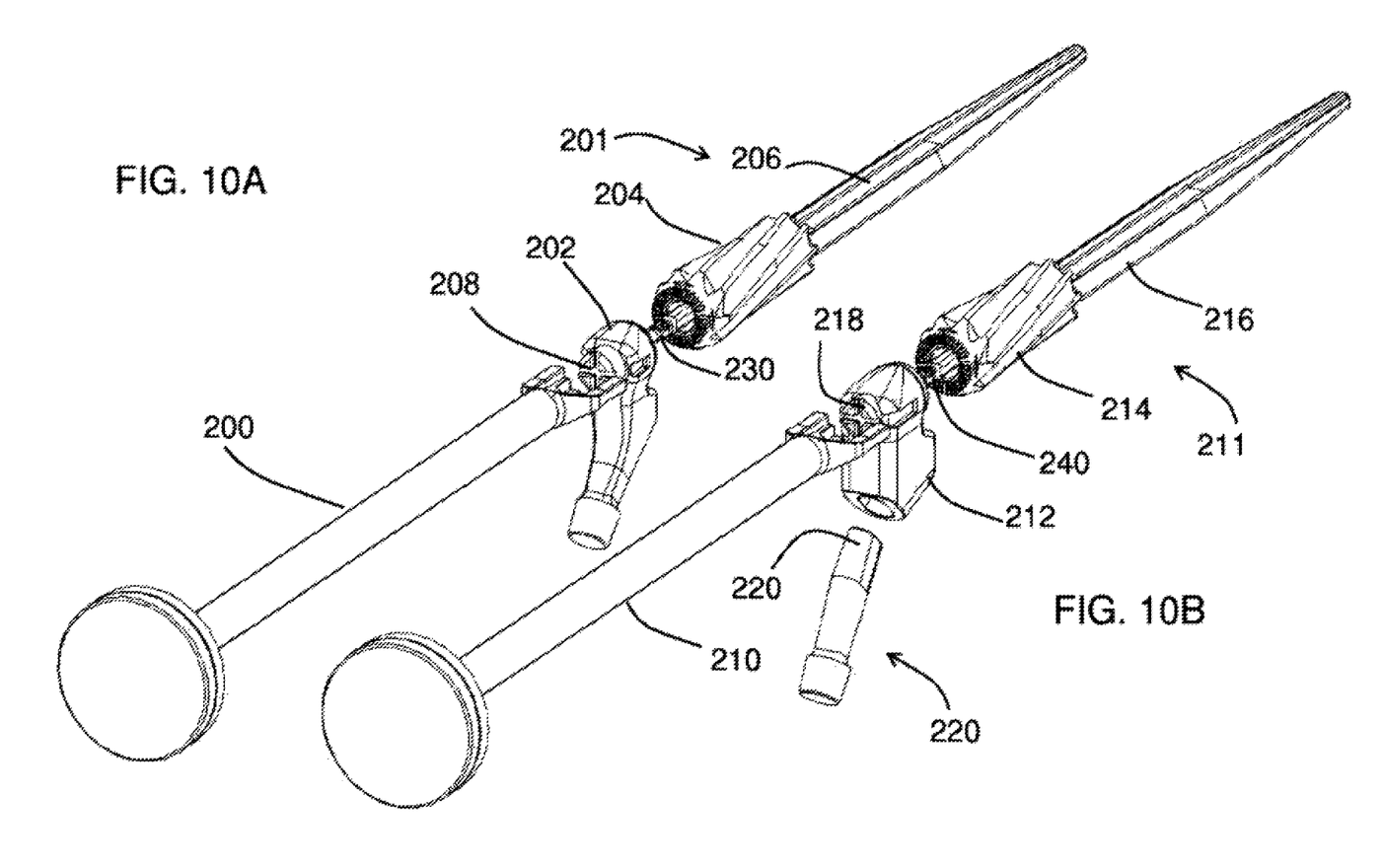
FIGS. 10A and 10B are exploded views of trial inserts and trial insertion tools according to an aspect of the invention.

Turning now to FIGS. 10A and 10B, FIGS. 10A and 10B are exploded views of trial inserts 201 and 211 and trial insertion tools 200 and 210 according to an embodiment of the invention. The trial inserts include a trial neck 202 and 212, a proximal reamer 204 and 214, distal reamer 206 and 216, and a connector 208 and 218. The trial 211 also includes a modular member 220 having a tapered portion 222 for insertion into the trial neck 212. The connectors 208 and 218 fix the trial neck 202 and 212 to the distal reamers 206 and 216 at the mounting tips 230 and 240.

In order to fine tune the anatomical fit of an implant, the modular member 220 is mated with the trial neck 218. The tapered portion 222 may adjust the geometrical length, height or angulation of the neck axis in order to restore the patient's anatomical kinesthetics. The tapered portion 222 may also have features that orient the neck relative to the bony anatomy, as mentioned above. The modular member 220 may be used on either an implant or trial.

The method of preparing the femoral canal includes attaching a distal cutting instrument to a drill. The cutting instrument is inserted into the IM canal and the distal portion is shaped by moving the distal cutting instrument in a first direction. When the distal portion is sufficiently shaped, then the drill is disconnected from the distal cutting instrument, and the distal cutting instrument may remain within the IM canal. A proximal cutting instrument is placed onto the distal cutting instrument over the shaft of the distal cutting instrument. The drill is then attached to the cutting instrument. In one embodiment, the drill is attached to the distal cutting instrument through a quick connect assembly. The proximal portion of the canal is shaped, and the canal may then be properly sized for an implant.

The method of preparing a trial insert includes shaping a distal portion by moving a first cutting instrument in a first direction and a proximal portion of a femur by moving a second cutting instrument in a second direction. A trial neck is attached to one of the cutting instruments. The trial neck is rotationally adjustable relative to the cutting instruments. A head of the trial neck may also be adjustable relative to the trial neck to adjust the version of the trial neck.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for preparing a femoral bone canal, comprising:
    inserting a distal cutting instrument into the femoral bone canal;
    rotating a shaft of the distal cutting instrument in a first rotational direction about a longitudinal axis of the distal cutting instrument thereby cutting a first portion of the femoral bone canal with a cutting portion of the distal cutting instrument;
    attaching a proximal cutting instrument to the shaft of the distal cutting instrument; and
    rotating the shaft of the distal cutting instrument to rotate the distal and proximal cutting instruments in a second rotational direction opposite the first rotational direction about the longitudinal axis thereby cutting a second portion of the femoral bone canal with the proximal cutting instrument without cutting the femoral bone canal with the distal cutting instrument;
    connecting a first mating surface of a trial neck to a second mating surface of the proximal cutting instrument via a splined connection, wherein the trial neck includes a base including the first mating surface and an arm extending from the base, wherein the first mating surface includes a first plurality of ridges and valleys and the second mating surface includes a second plurality of ridges and valleys adapted to mate with the first plurality of ridges and valleys, and wherein connecting the trial neck to the proximal cutting instrument comprises inserting the shaft of the distal cutting instrument through an aperture defined in the base of the trial neck; and
    securing the trial neck to the distal cutting instrument with a fastener at a proximal end of the trial neck.

2. The method of claim 1, wherein the first and second rotational directions are clockwise and counterclockwise rotation.

3. The method of claim 1, further comprising:
    rotating the trial neck relative to at least one of the distal and proximal cutting instruments; and
    fixing the trial neck to at least one of the distal and proximal cutting instruments.

4. The method of claim 1, wherein attaching the proximal cutting instrument to the shaft of the distal cutting instrument comprises attaching the proximal cutting instrument subsequent to cutting the first portion of the femoral bone canal.

5. The method of claim 1, wherein attaching the proximal cutting instrument to the shaft of the distal cutting instrument comprises attaching the proximal cutting instrument to the shaft of the distal cutting instrument such that rotational motion of the distal cutting instrument causes a corresponding rotational motion of the proximal cutting instrument in a same direction.

6. The method of claim 1, wherein attaching the proximal cutting instrument to the shaft of the distal cutting instrument comprises inserting the shaft of the distal cutting instrument through a bore defined in the proximal cutting instrument, wherein the shaft has a cross-sectional shape that is adapted to mate with a corresponding cross-sectional shape of the bore.

7. The method of claim 6, wherein the proximal cutting instrument is secured to the distal cutting instrument such that the proximal cutting instrument cannot rotate about the longitudinal axis relative to the distal cutting instrument when the proximal cutting instrument is attached to the distal cutting instrument.

8. The method of claim 1, wherein each of the distal and proximal cutting instruments is integrally formed to provide a single-piece unitary instrument.

9. The method of claim 1, further comprising:
removing the proximal cutting instrument from the distal cutting instrument;
attaching a cutting broach to the shaft of the distal cutting instrument to align the cutting broach with the longitudinal axis; and
moving the cutting broach along the longitudinal axis to make a rotationally asymmetric cut to the second portion of the femoral bone canal.

10. The method of claim 1, further comprising rotating the trial neck about the longitudinal axis relative to the proximal cutting instrument using a tool having prongs that grip recesses defined in an outer surface of the trial neck.

11. The method of claim 1,
further comprising preventing rotation of the trial neck relative to the femoral bone canal beyond a predefined point by an anti-rotational element of the trial neck.

12. The method of claim 1, wherein a shoulder of the shaft of the distal cutting instrument defines a maximum distance in a distal direction along the longitudinal axis that the proximal cutting instrument can travel along the shaft.

13. A method, comprising:
inserting a distal reamer into a femoral bone canal;
rotating a shaft of the distal reamer in a first rotational direction about a longitudinal axis defined by the distal reamer, wherein the distal reamer includes a cutting portion having flutes adapted to cut the femoral bone canal when the distal reamer is rotated in the first rotational direction but not cut the femoral bone canal when the distal reamer is rotated in a second rotational direction opposite the first rotational direction;
attaching a proximal reamer to the shaft of the distal reamer such that the shaft passes through a bore defined in the proximal reamer, wherein the proximal reamer includes flutes adapted to cut the femoral bone canal when the proximal reamer is rotated in the second rotational direction but not cut the femoral bone canal when the proximal reamer is rotated in the first rotational direction;
rotating the shaft of the distal reamer in the second rotational direction to cause rotation of the proximal reamer in the second rotational direction;
connecting a first mating surface of a trial neck to a second mating surface of the proximal reamer via a splined connection, wherein the trial neck includes a base including the first mating surface and an arm extending from the base, wherein the first mating surface includes a first plurality of ridges and valleys and the second mating surface includes a second plurality of ridges and valleys adapted to mate with the first plurality of ridges and valleys, and wherein connecting the trial neck to the proximal reamer comprises inserting the shaft of the distal reamer through an aperture defined in the base of the trial neck; and
securing the trial neck to the distal reamer with a fastener at a proximal end of the trial neck.

14. The method of claim 13, wherein the first rotational direction is a clockwise rotational direction.

15. The method of claim 13, wherein rotating the shaft of the distal reamer in the first rotational direction causes the distal reamer to cut a distal portion of the femoral bone canal; and
wherein rotating the shaft of the distal reamer in the second rotational direction causes the proximal reamer to cut a proximal portion of the femoral bone canal.

* * * * *